United States Patent
Bao et al.

(10) Patent No.: US 8,993,818 B2
(45) Date of Patent: *Mar. 31, 2015

(54) COMBINATION OF ZEOLITE UPGRADING WITH HYDROGENATION UPGRADING TO PRODUCE RENEWABLE GASOLINE FROM BIOMASS

(75) Inventors: Yun Bao, Bartlesville, OK (US); Edward L. Sughrue, II, Bartlesville, OK (US); Jianhua Yao, Bartlesville, OK (US); TiePan Shi, Bartlesville, OK (US); Kristi A. Fjare, Bartlesville, OK (US); Lisa L. Myers, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/214,508

(22) Filed: Aug. 22, 2011

(65) Prior Publication Data
US 2012/0095274 A1 Apr. 19, 2012

Related U.S. Application Data

(60) Provisional application No. 61/393,225, filed on Oct. 14, 2010.

(51) Int. Cl.
*C07C 1/20* (2006.01)
*B01J 23/882* (2006.01)
(Continued)

(52) U.S. Cl.
CPC .................. *C07C 1/20* (2013.01); *B01J 23/882* (2013.01); *B01J 23/883* (2013.01);
(Continued)

(58) Field of Classification Search
USPC ......... 585/319, 240, 250, 275, 276, 277, 310, 585/640, 733
See application file for complete search history.

(56) References Cited

U.S. PATENT DOCUMENTS

| 4,097,367 A | 6/1978 | Haag et al. |
| 4,503,278 A | 3/1985 | Chen et al. |

(Continued)

FOREIGN PATENT DOCUMENTS

| EP | 0366138 | 5/1990 |
| WO | 2008109877 | 9/2008 |

(Continued)

OTHER PUBLICATIONS

PCT Notification of Transmittal of the International Search Report and the Written Opinion of the International Searching Authority, or the Declaration, International Application No. PCT/US2011/048626; International Filing Date: Aug. 22, 2011, 12 pages.

*Primary Examiner* — In Suk Bullock
*Assistant Examiner* — Philip Louie
(74) *Attorney, Agent, or Firm* — Phillips 66 Company

(57) ABSTRACT

Technologies to convert biomass to liquid hydrocarbon fuels are currently being developed to decrease our carbon footprint and increase use of renewable fuels. Since sugars/sugar derivatives from biomass have high oxygen content and low hydrogen content, coke becomes an issue during zeolite upgrading to liquid hydrocarbon fuels. A self-sustainable process was designed to reduce the coke by co-feeding sugars/sugar derivatives with the paraffin products from hydrogenation of sugars/sugar derivatives. Paraffins without complete conversion result in products with less aromatics and relatively low density compared with the products directly from zeolite upgrading. Thus, the process is more economically favorable.

14 Claims, 1 Drawing Sheet

(51) Int. Cl.
  *B01J 23/883* (2006.01)
  *B01J 23/887* (2006.01)
  *B01J 29/40* (2006.01)
  *C10G 3/00* (2006.01)

(52) U.S. Cl.
  CPC ............. *B01J 23/8877* (2013.01); *B01J 29/40* (2013.01); *C07C 2521/02* (2013.01); *C07C 2521/04* (2013.01); *C07C 2521/06* (2013.01); *C07C 2523/06* (2013.01); *C07C 2523/26* (2013.01); *C07C 2523/28* (2013.01); *C07C 2523/42* (2013.01); *C07C 2523/44* (2013.01); *C07C 2523/46* (2013.01); *C07C 2523/72* (2013.01); *C07C 2523/75* (2013.01); *C07C 2523/755* (2013.01); *C07C 2523/80* (2013.01); *C07C 2523/86* (2013.01); *C07C 2523/882* (2013.01); *C07C 2523/883* (2013.01); *C07C 2525/02* (2013.01); *C07C 2527/10* (2013.01); *C07C 2531/20* (2013.01); *C07C 2531/22* (2013.01); *C07C 2531/24* (2013.01); *C10G 3/45* (2013.01); *C10G 3/47* (2013.01); *C10G 3/49* (2013.01); *C10G 3/50* (2013.01); *C10G 2300/202* (2013.01); *C10G 2400/02* (2013.01); *C10G 3/00* (2013.01); *C10G 3/46* (2013.01); *C10G 2300/1014* (2013.01); *C10G 2300/1018* (2013.01)

USPC .......... 585/319; 585/240; 585/640; 585/733; 585/310; 585/250; 585/275; 585/276; 585/277

(56) References Cited

U.S. PATENT DOCUMENTS

| | | | |
|---|---|---|---|
| 4,549,031 A | 10/1985 | Chen et al. | |
| 4,690,903 A | 9/1987 | Chen et al. | |
| 5,336,819 A | 8/1994 | McAuliffe et al. | |
| 5,841,678 A | 11/1998 | Hasenberg et al. | |
| 6,090,990 A | 7/2000 | Yao et al. | |
| 6,497,856 B1 * | 12/2002 | Lomax et al. | 423/651 |
| 7,550,634 B2 | 6/2009 | Yao et al. | |
| 7,678,950 B2 | 3/2010 | Yao et al. | |
| 8,450,542 B2 * | 5/2013 | Yao et al. | 585/240 |
| 8,552,230 B2 * | 10/2013 | Yao et al. | 585/3 |
| 2007/0135316 A1 * | 6/2007 | Koivusalmi et al. | 508/216 |
| 2009/0255171 A1 | 10/2009 | Dumesic et al. | |
| 2009/0283442 A1 * | 11/2009 | McCall et al. | 208/15 |
| 2010/0099933 A1 | 4/2010 | Yao et al. | |
| 2011/0046423 A1 * | 2/2011 | Sughrue et al. | 585/240 |
| 2011/0152513 A1 | 6/2011 | Yao et al. | |

FOREIGN PATENT DOCUMENTS

| | | |
|---|---|---|
| WO | 2011025632 | 3/2011 |
| WO | 2011078909 | 6/2011 |
| WO | 2011139551 | 11/2011 |

\* cited by examiner

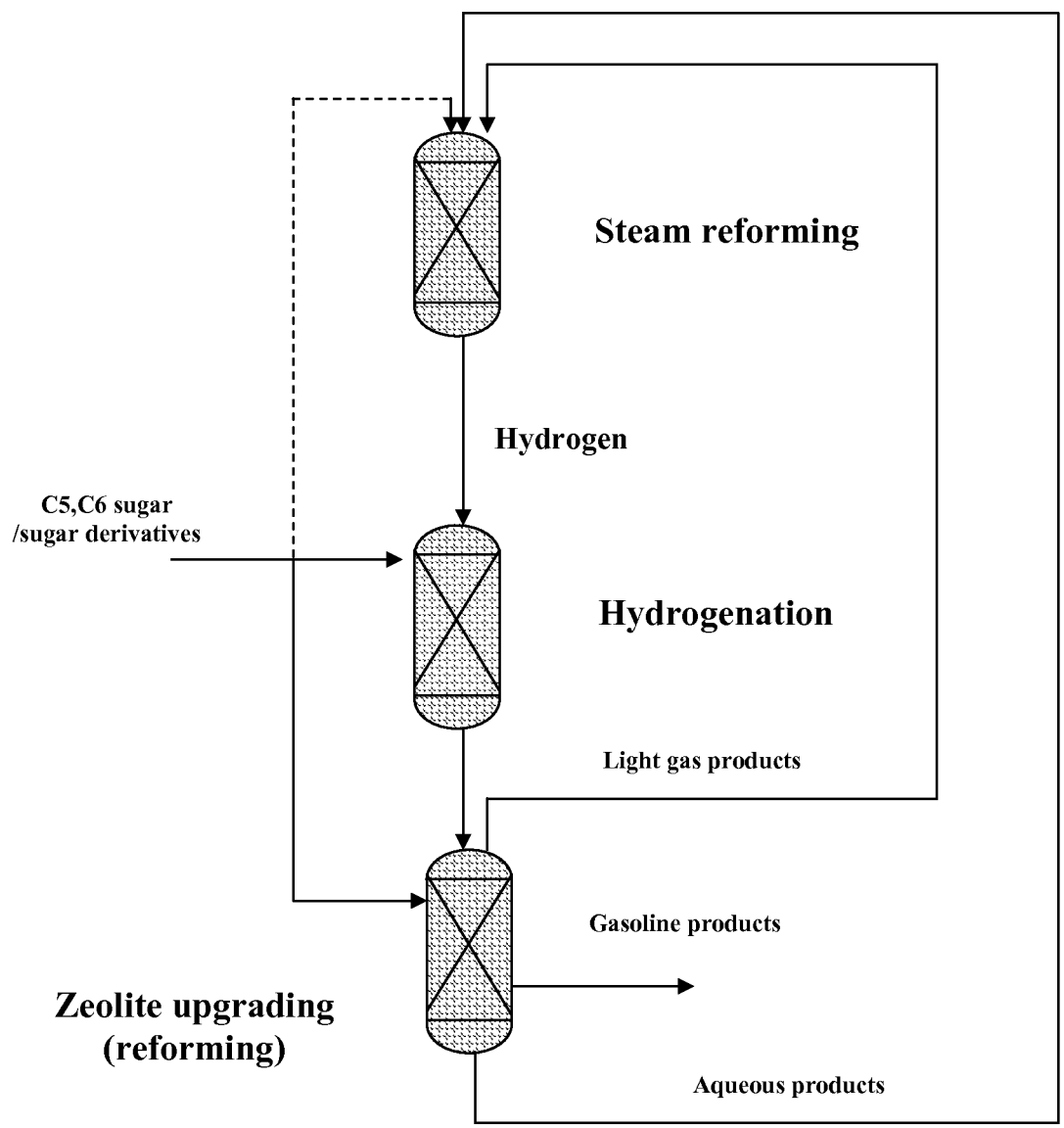

COMBINATION OF ZEOLITE UPGRADING WITH HYDROGENATION UPGRADING TO PRODUCE RENEWABLE GASOLINE FROM BIOMASS

CROSS-REFERENCE TO RELATED APPLICATIONS

This application is a non-provisional application which claims benefit under 35 USC §119(e) to U.S. Provisional Application Ser. No. 61/393,225 filed Oct. 14, 2010, entitled "COMBINATION OF ZEOLITE UPGRADING WITH HYDROGENATION UPGRADING TO PRODUCE RENEWABLE GASOLINE FROM BIOMASS," which is incorporated herein in its entirety.

STATEMENT REGARDING FEDERALLY SPONSORED RESEARCH OR DEVELOPMENT

None

FIELD OF THE INVENTION

The present invention relates generally to the conversion of biomass to fuel range hydrocarbons.

BACKGROUND OF THE INVENTION

Technologies to convert biomass to liquid hydrocarbon fuels are currently being developed to decrease our carbon footprint and increase use of renewable fuels.

Cellulose and hemicellulose are two major constituents in the biomass and can be broken down to C6 and C5 sugars using an acid or enzyme hydrolysis process. C6 and C5 sugars can be further converted to sugar alcohols or other derivatives. The sugars and their derivatives can be upgraded to gasoline range hydrocarbons, mainly aromatics, using a ZSM-5 catalyst, hydrotreating or combinations of ZSM-5 and hydrotreating.

However, the sugars and sugar derivatives from biomass have high oxygen content and low hydrogen content, and coking and frequently lower liquid yield becomes an issue during zeolite upgrading to liquid hydrocarbon fuels.

Addition of hydrogen donors with high effective hydrogen to carbon ratio such as methanol (U.S. Pat. No. 4,503,278) and i-pentane (U.S. Pat. No. 7,678,950) have been used to decrease coking, incorporated by reference. However, the cost to use methanol is high.

Therefore, developing a new process for converting sugar and sugar derivatives from biomass with reduced coking issue during zeolite upgrading to liquid hydrocarbon fuels would be a significant contribution to the art. In addition, development of a process for converting sugar and sugar derivatives to hydrocarbons which yields significant quantities of desirable hydrocarbon products such as aromatics and olefins would also be a significant contribution to the art.

BRIEF SUMMARY OF THE DISCLOSURE

A self-sustainable process is designed to reduce the coke by co-feeding sugars/sugar derivatives with the paraffin products from hydrogenation of sugars/sugar derivatives. Paraffins without complete conversion result in products with less aromatics and relatively low density compared with the products formed directly from zeolite upgrading. In addition, pentane and hexane have low vapor pressure and low octane number. By the combination of zeolite upgrading with hydrotreating upgrading, gasoline with an appropriate vapor pressure and octane number can be produced. Thus, the process is more economically favorable. This process may be used to upgrade the carbohydrate starting material to a gasoline range fuel product.

In one aspect of the current invention, a system for producing gasoline from biomass is described comprising a) a feedstock stream comprising sugars, sugar derivatives, polyols and carbohydrates, b) a hydrotreater to convert the feedstock to paraffins in the presence of hydrogen, c) a catalytic upgrader to convert the feedstock and the paraffins into a mixture product, d) a separator to separate the mixture product into a light gas stream, an aqueous stream and an organic stream, and e) a reformer to generate the hydrogen from at least one member selected from the group consisting of the light gas stream, the aqueous stream, the feedstock stream, and any combination thereof.

In another aspect of the current invention, a self-sustained process for producing gasoline from biomass is proposed where a feedstock comprising sugars, sugar derivatives, polyols and other carbohydrates can be co-fed with a hydrotreated product comprising paraffins from hydrogenation of the feedstock as hydrogen donor for zeolite upgrading to produce renewable gasoline. Products from zeolite upgrading may be separated as an aqueous stream, an organic stream and a light gas stream (such as $CH_4$, $C_2H_6$). The organic stream comprises gasoline range hydrocarbons, mainly aromatics. The light gas stream, and/or a portion of feedstock comprising sugars, sugar derivatives, polyols and other carbohydrates, and/or any aqueous products from the zeolite reforming process can be used to generate hydrogen by steam reforming. The generated hydrogen will be used for hydrotreating the feedstock.

The feedstock comprising sugars, sugar derivatives, polyols and other carbohydrates may be derived from biological materials including sugars, monosaccharides, polysaccharides, glyceraldehyde, erythritol, xylitol, sorbitol, dextrose, glucose, fructose, galactose, glycerol, glycerin, carbohydrates, sucrose, maltose, lactose, cellobiose, melibiose, raffinose, starch, corn stover, algae, switchgrass, soybean, vegetable matter, and animal fats.

Zeolite catalysts can include $SiO_2$, $Al_2O_3$, ZSM-5, ZSM-8, ZSM-11, ZSM-12, ZSM-35, ZSM-38, MFI, Pentasil, HZSM-5, T-4480, and the like, the catalysts may be combined as required to achieve specific product specifications.

The separators include gas-liquid, liquid-liquid, three-phase, horizontal, vertical, tubular, rotary, turbine, centrifugal, and any combination thereof.

Reformer catalysts include nickel impregnated aluminum oxide (Ni/$Al_2O_3$), nickel impregnated magnesium oxide (Ni/MgO), platinum impregnated aluminum oxide (Pt/$Al_2O_3$), platinum impregnated magnesium oxide (Pt/MgO), and catalyst impregnated ceramic pellets, modified ceramics, metal foils, and combinations thereof.

Hydrotreater catalysts include nickel, aluminum, hafnium, platinum, palladium, ruthenium, nickel, palladium (II) acetate trimer, palladium (II) chloride, sodium tetrachloropalladate (II), tetrakis(triphenylphosphine)palladium (0), dihydrogen hexachloroplatinate (IV), platinum (II) chloride, platinum (IV) chloride, potassium tetrachloroplatinate (II), chloro(1,5-cyclooctadiene)rhodium (I) dimer, chlorotris(triphenylphosphine)rhodium (I), rhodium (II) acetate dimer, rhodium (III) chloride hydrate, ruthenium (III) chloride trihydrate, iridium (III) chloride hydrate, osmium (VIII) tetroxide, rhenium carbonyl ($Re_2(CO)_{10}$), organophosphines, nickel, copper impregnated zinc oxide (Cu/ZnO), copper impregnated chromium oxide (Cu/Cr), nickel aluminum oxide (Ni/Al$_2$O$_3$), palladium aluminum oxide (Pd/Al$_2$O$_3$), cobalt molybdenum (CoMo), nickel molybdenum (NiMo), and combinations thereof.

BRIEF DESCRIPTION OF THE DRAWINGS

FIG. 1 is a schematic diagram illustrating a process for the combination of zeolite upgrading and hydrogenation upgrading to produce renewable gasoline from biomass.

DETAILED DESCRIPTION OF THE EMBODIMENTS OF THE INVENTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

According to the embodiments of the current invention, there is provided a self-sustainable process and system for producing gasoline from biomass. A feedstock stream comprising sugars, sugar derivatives, polyols and carbohydrate was hydrotreated in a hydrotreater to produce paraffins in the presence of hydrogen. The paraffins are then used as hydrogen donors and co-fed with the feedstock into a catalytic upgrader wherein the feedstock and parafins are converted into a mixture product. The mixture product is then being separated by a separator into a light gas stream, an aqueous stream and an organic stream. The light gas stream, and/or the aqueous stream, and/or the feedstock stream are then fed into a reformer to produce hydrogen to use for the feedstock hydrotreating process as described above. This self-sustainable process was designed to reduce coke. Paraffins without complete conversion result in products with less aromatics and relatively low density compared with the products formed directly from zeolite upgrading. Thus, the process is more economically favorable. This process may be used to upgrade the carbohydrate starting material to a gasoline range fuel product. In addition, pentane and hexane have a low vapor pressure and low octane number. By the combination of zeolite upgrading with hydrotreating upgrading, gasoline with an appropriate vapor pressure and octane number can be produced.

The feedstock may comprise sugars, sugar derivatives, polyols and other carbohydrates derived from biological materials including sugars, monosaccharides, polysaccharides, glyceraldehyde, erythritol, xylitol, sorbitol, dextrose, glucose, fructose, galactose, glycerol, glycerin, carbohydrates, sucrose, maltose, lactose, cellobiose, melibiose, raffinose, starch, corn stover, algae, switchgrass, soybean, vegetable matter, and animal fats.

Carbohydrates, such as starches and sugars may be converted in accordance with the present invention to form a hydrocarbon mixture useful for liquid fuels and chemicals. The term, "carbohydrate" is used generally to refer to a compound of carbon, hydrogen and oxygen having the general formula $C_x(H_2O)_y$, in which the ratio of hydrogen to oxygen is the same as in water. Carbohydrates include monosaccharides, polysaccharides, and mixtures of monosaccharides and/or polysaccharides. The term "monosaccharide" or "monosaccharides" includes compounds that are generally hydroxy aldehydes or hydroxy ketones which cannot be hydrolyzed into any simpler carbohydrate. Monosaccharides can be a triose with 3 carbon atoms, tetrose with 4 carbon atoms, pentose with 5 carbon atoms, hexose with 6 carbon atoms, or larger monosaccharides like sedoheptulose with 7 carbon atoms or neuraminic acid with 9 carbon atoms. Examples of monosaccharides include glyceraldehyde, erythrose, xylose, dextrose, glucose, fructose and galactose. The term "polysaccharide" or "polysaccharides" includes those saccharides containing more than one monosaccharide unit. This term also includes disaccharides (such as sucrose, maltose, cellobiose, and lactose) and oligosaccharides.

Carbohydrate feedstock comprises a mixture of one or more carbohydrate derivatives including polysaccharides, monosaccharides, polyols, sugars and sugar alcohols from a variety of sources, as well as other byproducts of biological degradation that are not removed as solids or are not completely removed by other processes. In some examples a single polyol, such as sorbitol or xylitol in aqueous solution is used as a carbon feedstock. In another embodiment, a mixed solution containing a natural byproduct such as acid hydrolyzed corn stover is used as a feedstock. Acid hydrolyzed corn stover may contain sorbitol, xylitol, furfural, hydroxymethyl furfural, levulinic acid or esters, polysaccharides, disaccharides, and monosaccharides as well as other degradation products. In another embodiment, insoluble starch (e.g., cornstarch) is used as the starting material. Starch, in its native form has two structural classes: amylose and amylopectin that is suspended in water and liquefied in the presence of acid and/or enzymes that convert the starch first, to a mixture of glucose, maltose, and higher saccharides then to a corn syrup mixture of glucose, maltose, and maltodextrins. Any number of biological and chemical pathways may be used with a variety of source materials to generate mixed carbohydrate feedstocks for conversion to hydrocarbons.

Examples of carbohydrates useful as starting materials in accordance with the present invention include, but are not limited to, polysaccharides such as sucrose, maltose, lactose, cellobiose, melibiose, raffinose, starch (derived from a variety of cereal grains such as wheat and rice, tubers such as potato, tapioca, and arrowroot, or waxy starches such as waxy moil and maize) and starch decomposition products such as dextrin and corn syrup (also known as glucose syrup).

Carbohydrates useful in the present invention may be dissolved in any aqueous reaction medium, including water. In addition reaction of carbohydrates with ion-exchange resins in accordance with U.S. Pat. No. 7,678,950, may be carried out in any suitable apparatus that enables intimate contact of the reactants and control of the operating conditions. The process may be carried out in batch, semi-continuous, or continuous operation. In one embodiment, a batch operation in a conventional autoclave is used.

The feedstock is fed into a hydrotreater in the presence of hydrogen for a hydrogenation reaction to occur. The hydrogenation reaction, as shown in but not limited to the reaction in U.S. Pat. No. 5,841,678, can be accomplished with numerous commercially available hydrotreating catalysts, with or without nitrogen in the presence of hydrogen. Temperatures may be optimized depending upon the size of the hydrocarbons, contaminants present, and activity of the hydrotreating catalyst. Some of the numerous hydrotreating catalysts include MoS$_2$ and NiMo. The reaction may be carried out at elevated temperatures and elevated pressures depending upon the reaction required. In one embodiment, the hydrotreating reaction is carried out at approximately 350° C. and about 3 MPa or approximately 450 psig. Typically reactions are maintained between 200° C. and 500° C. In one embodiment the temperature 250 to about 400° C., and reactor pressures from about 100 to about 2000 psig, preferably in the range of about 300 to about 1500 psig.

Hydrogenation reactions can also be accomplished by non-sulfided catalysts such as noble metals or nickel metal catalysts under hydrogen pressure. Typical noble metal catalysts are based on aluminum, hafnium, platinum, palladium, ruthenium or combinations thereof, with or without promoter supported metal oxides or carbon. Examples of hydrogenation catalysts include nickel, palladium (II) acetate trimer, palladium (II) chloride, sodium tetrachloropalladate (II), tetrakis(triphenylphosphine) palladium (0), dihydrogen hexachloroplatinate (IV), platinum (II) chloride, platinum (IV) chloride, potassium tetrachloroplatinate (II), chloro(1,5-cyclooctadiene)rhodium (I) dimer, chlorotris(triphenylphosphine) rhodium (I), rhodium (II) acetate dimer, rhodium (III) chloride hydrate, ruthenium (III) chloride trihydrate, iridium (III) chloride hydrate, osmium (VIII) tetroxide, rhenium carbonyl ($Re_2(CO)_{10}$), organophosphines, nickel, copper impregnated zinc oxide (Cu/ZnO), copper impregnated chromium oxide (Cu/Cr), nickel aluminum oxide (Ni/$Al_2O_3$), palladium aluminum oxide (Pd/$Al_2O_3$), cobalt molybdenum (CoMo), nickel molybdenum (NiMo), and the like. The hydrogenation metal may be supported on a metal support, metal oxides, ceramics or carbon with or without various promoters. Reaction temperatures could range from about 80° C. to about 400° C., including preferably between approximately 250° C. to 350° C. range. Reactions temperatures may be approximately 75° C. to 425° C. with a range of 25° C. to 50° C. Hydrogen pressures range from about 200 psig to 2500 psig, typically including in the range of 600-1500 psig. Reaction pressures may be between approximately 200-2500 psig with a variation of 100 to 150 psig or approximately 10%-20% variation in psig. The hydrogenation reaction hydrogenates sugars, sugar derivatives, polyols and other carbohydrates derived from biological materials to produce paraffins such as pentane and hexane. The oxygen atoms in the feedstocks are removed as mainly water with a small amount of carbon monoxide and carbon dioxide. The paraffins are then co-fed with the feedstock into a catalytic upgrader wherein the feedstock and paraffins are converted into a mixture product. The presence of the hydrogenated feedstock including paraffins serves as a hydrogen donor and contributes to upgrading of the feedstock, improving removal of hydroxyls from the carbohydrates to form more hydrocarbons and water and less $CO_2$ thus reducing coking and fouling of the catalyst in the catalytic upgrader. Paraffins without complete conversion result in products with less aromatics and relatively low density compared with the products directly from zeolite upgrading. Thus, the process is more economically favorable.

Suitable zeolites include, but are not limited to, those disclosed in the Kirk-Othmer Encyclopedia of Chemical Technology (1981), incorporated herein by reference. Generally, zeolites useful in the present invention have a constraint index (as defined in U.S. Pat. No. 4,097,367, which is incorporated herein by reference) in the range of from about 0.4 to about 12, and preferably in the range of from about 2 to about 9. In addition, the molar ration of $SiO_2$ to $Al_2O_3$ in the crystalline framework of the zeolite is at least about 5:1 and can range up to infinity. In one embodiment of the present invention, the molar ratio of $SiO_2$ to $Al_2O_3$ in the crystalline framework of the zeolite is in the range of from about 8:1 to about 200:1. In another embodiment of the present invention, $SiO_2$ to $Al_2O_3$ in the crystalline framework of the zeolite is in the range of from about 12:1 to about 100:1.

Some zeolites useful in the present invention include but are not limited to ZSM-5, ZSM-8, ZSM-11, ZSM-12, ZSM-35, ZSM-38, $SiO_2$, $Al_2O_3$, and the like. The catalysts may be combined as required to achieve specific product specifications. Some of these zeolites are also known as "MFI" or "Pentasil" zeolites. In one example, the zeolite HZSM-5 purchased from UCI (United Catalysts, Inc., Louisville, Ky.) having a designate of T-4480 (obtained as a 1/16 inch extrudate) was used. Modified zeolites can also be used. Modified zeolites can include zeolites modified by metal cations, such as, for example, zinc, platinum, gallium, or nickel. Zeolites can also be modified by steam treatment, acid treatment, base treatment, as well as other treatments alone or in combination. In addition, zeolites of the present invention may be combined with a clay, promoter, and/or a binder. Zeolites useful in the present invention may also contain an inorganic binder (also referred to as matrix material) selected from the group consisting of alumina, silica, alumina-silica, aluminum phosphate, clays (such as bentonite), and combinations thereof. The type of zeolite used may cause the final product to vary dependent upon starting materials, reaction conditions, and length of reaction.

Hydrogenated products including paraffins such as pentane and hexane, can be used as hydrogen donors and to be co-fed with the feedstock stream into the zeolite reforming unit to produce a mixture product containing a variety of fuel range hydrocarbons, light gases, and an aqueous solution.

The flow rate may vary depending on the specific reaction conditions and include flow rates of approximately 1 to 30 up to about 1150 ml/hr for 8 grams of catalyst. In one embodiment of the present invention, the flow rate is between approximately 0.1 ml/hr to 25 ml/hr per gram of catalyst, preferably between 0.5 and 7.0 ml/hr per gram of catalyst. Thus, using the embodiments described above, 10 g of catalyst could be run with a flow rate between about 1 ml/hr and about 250 ml/hr, preferably between about 5 ml/hr and 70 ml/hr. The viscosity of the fluid, temperature of the reaction, and porosity of the catalyst can all influence the flow rate, under certain circumstances, low viscosity, higher temperatures, and increased catalyst porosity, the flow rate can be increased to about 30 ml/hr, 40 ml/hr, 50 ml/hr or up to 60 ml/hr per gram of catalyst.

The time of reaction will depend upon the specific starting material, concentration, the specific catalyst used, pressure and temperature. Generally, the liquid hourly space velocity is in the range of from about 0.1 to about 10 $hr^{-1}$, which may be lower or higher depending on the desired conversion. The reaction is carried out in any suitable type of apparatus or reaction chamber which enable intimate contact of the reactants and control of the operating conditions. The process may be carried out in batch, semi-continuous, or continuous operation. In one embodiment of the present invention, a batch operation in a conventional autoclave is used. The reactants may be added to the reaction chamber in any suitable manner or in any suitable order. In one embodiment of the present invention, the carbohydrate-containing solution is fed through the zeolite catalyst.

The light gas stream, an aqueous stream and an organic stream are then being separated in a separator. The separators include gas-liquid, liquid-liquid, three-phase, horizontal, vertical, tubular, rotary, turbine, centrifugal, and any combination thereof. For example a gas-liquid separation of light gases from a mixture of liquids followed by a liquid-liquid separator to separate the organic phase from the aqueous phase. Additional separations may be added to improve the purity/separation of the light gas stream, organic stream, or aqueous stream.

A variety of separators are available with different purposes and results. Phase separators, hydrocyclones, reflux columns, and the like may be used to separate with different sensitivities an organic stream, a light gas phase, and an aqueous phase. The amount of each stream will depend upon the initial feedstock and desired products. Increasing the size of the feedstock carbohydrates or recycle stream hydrocarbons will subsequently increase the size of the hydrocarbons in the organic stream. In one embodiment, a three phase separator with stainless steel or carbon steel material can be used to separate the gas stream, liquid stream and aqueous stream. The three phase separator may be horizontal, vertical, tubular, rotary, turbine, centrifugal, or other type of separator. Separators may be combined in a linear fashion to achieve better separation of mixed solutions, including separators to remove one or more components at each separation. A variety of three phase separators are available from Monarch Separators, Houston, Tex.; Pacific Process Systems (PPS) Inc., Bakersfield, Calif.; Douglas Energy Company, Placentia, Calif.; Process Equipment & Service Company, Inc., Farmington, N. Mex.; Petrex, Inc., Harvey, La.; Permian Tank & Manufacturing, Odessa, Tex.; Zhangjiagang Chemical Machinery Co., Ltd., Suzhou, Jiangsu, China; GEA Westfalia Separator, Cujik, Netherlands and others, or through construction of a custom three phase separator system. In another embodiment, an elutriation column is used to separate the oil and water mixture into a light carbon fraction (C1-05), an aqueous fraction containing water and water soluble components, and an organic stream containing gasoline range hydrocarbons from C5 to C13. Other separation techniques include using one or more pieces of equipment to separate hydrocarbons, aqueous liquids, and gases through any one of the three streams.

In one embodiment, an organic stream is separated from the remaining solution, leaving the aqueous stream, light gas stream, and any contaminants or partially converted feedstock to feed directly into the steam reformer. One with skill in the art may be able to separate out a variety of mixed hydrocarbons or remove several hydrocarbons with increased purity for further processing or sale.

Organic components in the organic stream include a variety of hydrocarbons, both linear and cyclic, containing carbons from C4 to C14 including saturated and unsaturated hydrocarbons with C4, C5, C6, C7, C8, C9, C10, C11, C12, C13 and C14 carbons. The organic stream may be separated out at this point to be used as a blending stock of high octane product.

Light gases include methane, ethane, butane, isobutane, propane, pentane, and mixtures thereof. Light gases produced during catalytic upgrading may be processed into individual or mixed products such as methane, ethane, propane, butane, compressed natural gas (CNG), natural gas liquids (NGL), liquefied petroleum gas (LPG), liquefied natural gas (LNG), or transferred to reforming for hydrogen generation with biomass solids (FIG. 1). Light gases, typically removed and burned off as a low value product, are now used to add value with a steam reformer that generates hydrogen from the light gases and aqueous solution.

Aqueous solution contains water and water soluble components including salts, hydrophilic solutions, other compounds, as well as any solid debris that may be washed through to the reformer. Because the carbohydrate feedstock may contain a large portion of aqueous solution and is typically dissolved in aqueous solution, water produced must be recycled, reprocessed, or purified prior to release. Feeding the aqueous solution to a steam reformer converts any contaminants and soluble matter into $CO_2$ and hydrogen with heat.

In addition, the product of the present invention may also contain byproducts of carbon monoxide and carbon dioxide ($CO_2$). By using the light gases and aqueous phase in a hydrogen reformer, large quantities of hydrogen are generated. This solves multiple problems and allows complete utilization of

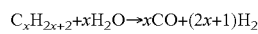

$$C_xH_{2x+2}+xH_2O \rightarrow xCO+(2x+1)H_2$$

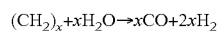

$$(CH_2)_x+xH_2O \rightarrow xCO+2xH_2$$

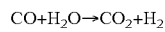

$$CO+H_2O \rightarrow CO_2+H_2$$

the refined products from the zeolite upgrader. First, contaminated water present from the carbohydrate solution is converted mole per mole to hydrogen. Light gases, previously burned off to recover heat, are now converted to $CO_2$ and additional hydrogen. The net result is that light gas hydrocarbons like methane ($CH_4$), ethane ($C_2H_6$), propane ($C_3H_8$) and any other gaseous hydrocarbons, as well as any solids, remaining polyols, or other gases from the light gas or aqueous feed are converted to gas and reformed at high temperatures. Each carbon in a paraffinic light gas converted with excess water in the reformer generates at least 3 moles of hydrogen, and ensures all of the products are used to upgrade the organic stream. All of the excess hydrogen generated is fed directly into the hydrotreater to convert any of a variety of carbon products to saturated hydrocarbons.

The aqueous stream and light gas stream are fed into the steam reformer. Any standard steam reforming catalyst may be used within the reformer. An exemplary steam reforming catalyst is nickel oxide on a low-silica refractory base. The steam reformer furnace may "stand alone", or operate in conjunction with a pre-reformer, post-reformer, or other schemes. In the furnace, the reforming of steam-hydrocarbon mixtures is accomplished in catalyst-filled tubes. In hydrogen plants, in-tube fluid pressures are typically 25-30 kg/cm2 with outlet temperatures of between about 700 to 1250° C. Typically temperatures may vary by 10° C., 20° C., up to 50° C. or more. A variety of catalysts are available for a given feed and product requirement including nickel, nickel/alumina, limestone, dolomite and iron ore. In one embodiment, the temperature is in the range of 760 to 816° C. for complete reforming with nickel oxide catalyst on a low-silica refractory base with a steady stream of steam and light gases. Other reformer catalysts with a variety of different catalyst types including nickel impregnated aluminum oxide ($Ni/Al_2O_3$), nickel impregnated magnesium oxide (Ni/MgO), platinum impregnated aluminum oxide ($Pt/Al_2O_3$), platinum impregnated magnesium oxide (Pt/MgO), catalyst impregnated ceramic pellets, modified ceramics, metal foils, and the like, that can be used in the reforming reaction described above. Steam reacts with the light gases to yield carbon monoxide and hydrogen. Heat from the hydrogenation step could be used to provide heat for steam reforming.

The following examples of certain embodiments of the invention are given. Each example is provided by way of explanation of the invention, one of many embodiments of the invention, and the following examples should not be read to limit, or define, the scope of the invention.

The experiments of different sugar compounds/sugar derivatives with pentane or hexane over ZSM-5 (T-4480 or modified T-4480) have been performed. Reaction was carried out at 450-500° C., 200 psig, catalyst loading was 8 g and sugar compounds/sugar derivatives feed rate was 10 ml/hr and pentane or hexane flow rate was 12 ml/hr. The experimental results are shown as follows:

EXAMPLE 1

In one example, as shown in Table 1, hexane is a major product from sorbitol feedstock hydrogenation. Hexane was co-fed with sorbitol over a zeolite upgrading catalyst. The reaction was carried out at 450° C., 200 psig, with 8 g ZSM-5.

The feed rates of sorbitol (70% sorbitol with 30% water) and hexane were 10 ml/hr and 12 ml/hr, respectively. Sorbitol conversion was 99%. The reaction products included greater than about 50% C5+ hydrocarbons with a high percentage of those hydrocarbons being aromatic (55.8%). The high aromatic content and large number of C5+ hydrocarbons led to a gasoline product with an approximate octane rating of 87-99. This is an ideal octane rating for high performance gasoline fuels and exceeds the required octane rating for "premium" gasoline in the United States and "superplus" gasoline in Europe. This experiment demonstrates that mixing a hydrogenated product, hexane, with the sorbitol feedstock produces a high octane gasoline quality fuel from a biological source material, sorbitol. In addition, as shown in Table I, the product contains a low amount of $CO_2$, a low amount of coke and few undesirable by products (Sorbitol was not run by itself. Sorbitol produces more coke than xylitol and ethyl levulinate).

TABLE 1

Sorbitol processing to gasoline hydrocarbons.

| Run ID | A |
|---|---|
| Sugar/derivative Molecules | Sorbitol |
| Hydrogen donor | Hexane |
| T(° C.) | 450 |
| Catalyst Description | ZSM-5 |
| Product selectivity (wt %) | |
| $C_1$-$C_4$ Paraffins | 31.92 |
| $C_2$-$C_4$ olefins | 4.11 |
| $C_5$+ | 42.92 |
| $CO + CO_2$ | 15.31 |
| Coke | 5.74 |
| Coke on Cat. | 3.05 |
| Aromatics content in $C_5$+ fraction (wt %) | 55.8 |
| Octane number of C5+ fraction | 86.6 |

EXAMPLE 2

The process in example 1 was repeated with xylitol (50 wt % aqueous solution) instead of sorbitol. The same process conditions were used, the reaction was carried out at 450° C. (or 500° C.) 200 psig, with 8 g ZSM-5. Xylitol (50% xylitol with 50% water) and pentane were fed at rates of 10 ml/hr and 12 ml/hr, respectively. Xylitol conversion was 99%. The reaction products included about 50% C5+ hydrocarbons and an octane rating of 107. This high octane rating makes the fuel ideal for blending to increase the octane of fuels with lower octane ratings. Additionally, the high levels of conversion with xylitol indicate that polyols in general can be converted to gasoline quality fuels with high octane ratings of nearly 100 or greater than 100 from biological feedstocks comprising polyols and water. In addition, as shown in Table 2, the hydrocarbon product contains a low amount of $CO_2$, low amount of coke and few undesirable by products. Xylitol (50% xylitol with 50% water) was fed at rates of 16 ml over 8 g ZSM-5. The reaction the reaction was carried out at 450° C., 200 psig. The results are compared in Table 2.

TABLE 2

Xylitol processing to gasoline hydrocarbons.

| Run ID | B | | |
|---|---|---|---|
| Sugar/derivative Molecules | Xylitol | Xylitol | Xylitol |
| Hydrogen donor | Pentane | Pentane | |
| T(° C.) | 500 | 450 | 450 |
| Catalyst Description | ZSM-5 | ZSM-5 | ZSM-5 |
| Product selectivity (wt %) | | | |
| $C_1$-$C_4$ Paraffins | 42.72 | 39.79 | 4.84 |
| $C_2$-$C_4$ olefins | 5.48 | 2.89 | 3.93 |
| $C_5$+ | 37.49 | 45.34 | 43.55 |
| $CO + CO_2$ | 12.65 | 10.58 | 39.95 |
| Coke | 1.66 | 1.40 | 7.73 |
| Coke on Cat. | 1.40 | 1.30 | 6.38 |
| Aromatics content in $C_5$+ fraction(wt %) | 79.7 | 72.1 | 83.2 |
| Octane number of C5+ fraction | 107.0 | 103.6 | 107.0 |

EXAMPLE 3

The process in example 1 was repeated with ethyl levulinate (100% ethyl levulinate) instead of sorbitol or xylitol. The same process conditions were used, the reaction was carried out at 450° C., 200 psig, with 8 g ZSM-5, and ethyl levulinate and pentane were fed at rates of 10 ml/hr and 12 ml/hr, respectively. Ethyl levulinate was completely converted. The reaction products included about 50% C5+ hydrocarbons and had an octane rating of 103.9. This high octane rating makes the fuel ideal for blending to increase the octane of fuels with lower octane rating$_s$. Additionally, the high level of conversion with ethyl levulinate indicate that polyols in general can be converted to gasoline quality fuels with high octane ratings of nearly 100 or greater than 100 from biological feedstocks comprising polyols and water. In addition, as shown in Table I, the hydrocarbon product contains a low amount of $CO_2$, a low amount of coke and few undesirable by products. Ethyl levulinate was fed at rates of 22 ml over 8 g ZSM-5. The reaction the reaction was carried out at 450° C., 200 psig. The results are compared in Table 3.

TABLE 3

Ethyl levulinate processing to gasoline hydrocarbons.

| Run ID | C | |
|---|---|---|
| Sugar/derivative Molecules | Ethyl levulinate | Ethyl levulinate |
| Hydrogen donor | Hexane | |
| T(° C.) | 450 | 450 |
| Catalyst Description | ZSM-5 | ZSM-5 |
| Product selectivity (wt %) | | |
| $C_1$-$C_4$ Paraffins | 36.52 | 6.52 |
| $C_2$-$C_4$ olefins | 1.05 | 8.95 |
| $C_5$+ | 46.16 | 50.47 |
| $CO + CO_2$ | 13.23 | 26.95 |
| Coke | 3.04 | 7.11 |
| Coke on Cat. | 3.04 | 5.50 |
| Aromatics content in $C_5$+ fraction (wt %) | 76.6 | 70.1 |
| Octane number of C5+ fraction | 103.9 | 101.4 |

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein.

It is the intent of the inventors that variations and equivalents of the invention are within the scope of the claims while the description, abstract and drawings are not to be used to limit the scope of the invention. The invention is specifically intended to be as broad as the claims below and their equivalents. In closing, it should be noted that each and every claim below is hereby incorporated into this detailed description or specification as an additional embodiments of the present invention.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:

1. U.S. Pat. No. 4,503,278 "Process for converting carbohydrates to hydrocarbons," Chen & Koenig, Mobil Oil Corp.
2. U.S. Pat. No. 4,097,367, "Conversion of olefinic naphtha," Haag & Huang, Mobil Oil Corp.
3. U.S. Pat. No. 5,841,678, "Modeling and simulation of a reaction for hydrotreating hydrocarbon oil," Hasenberg & Campagnolo, ConocoPhillips Co.
4. U.S. Pat. No. 6,090,990, "Method of making an improved catalyst containing zeolite treated with boron trichloride, the product from such method, and the use thereof in the conversion of hydrocarbons".
5. U.S. Pat. No. 7,678,950, US2007142633, WO2007075370 "Process for converting carbohydrates to hydrocarbons," Yao, et al., ConocoPhillips Co.
6. U.S. Pat. No. 4,549,031 "Process for converting carbohydrates to hydrocarbons," Chen & Koenig, Mobil Oil Corp.
7. U.S. Pat. No. 7,550,634 "Process for converting triglycerides to hydrocarbons," Yao, et al., ConocoPhillips Co.
8. U.S. Pat. No. 5,336,819 "Process for preparing organic fuels and chemicals from biomass," McAuliffe & Benn, Man Oil Ltd.
9. U.S. Ser. No. 12/644,438, "Integrated Process for Converting Carbohydrates to Hydrocarbons," Yao, et al., ConocoPhillips Co.
10. U.S. Ser. No. 61/236,347, "Hydrotreating Hydrocarbons," Sughrue, et al., ConocoPhillips Co.
11. U.S. Ser. No. 61/288,912, "Conversion of Carbohydrates to Hydrocarbons," Yao, et al., ConocoPhillips Co.
12. EP0366138, "Process for manufacturing fuel from ligno-cellulose material," Jelks & Strouth.

What is claimed is:

1. A system for producing gasoline from biomass comprising:
    a) a feedstock stream comprising at least one member selected from the group consisting of sugars, sugar derivatives, polyols and carbohydrates,
    b) a hydrotreater configured to convert a first portion of said feedstock stream to paraffins in the presence of hydrogen and a hydrotreating catalyst,
    c) a catalytic upgrader comprising a zeolite catalyst and configured to receive and convert a second portion of said feedstock stream and said paraffins into a mixture product,
    d) a separator configured to receive and separate said mixture product into a light gas stream, an aqueous stream and an organic stream, and
    e) a reformer configured to receive at least one stream selected from the group consisting of said light gas stream, said aqueous stream and a third portion of said feedstock stream, and generate said hydrogen from said at least one stream.

2. A process for producing gasoline from biomass comprising:
    a) providing a feedstock stream comprising at least one member selected from the group consisting of sugars, sugar derivatives, polyols and carbohydrates,
    b) hydrotreating a first portion of said feedstock stream in a hydrotreater to produce paraffins in the presence of hydrogen and a hydrotreating catalyst,
    c) co-feeding a second portion of said feedstock stream and said paraffins into a catalytic upgrader comprising a zeolite catalyst and converting said second portion of said feedstock stream and said paraffins into a mixture product,
    d) separating said mixture product into a light gas stream, an aqueous stream and an organic stream in a separator, wherein said organic stream comprises gasoline-range hydrocarbons having an octane rating of at least 86, and
    e) reforming at least one stream selected from the group consisting of said light gas stream, said aqueous stream and a third portion of the feedstock stream, to generate said hydrogen.

3. The system of claim 1, wherein said feedstock stream comprises at least one of monosaccharides, disaccharides, polysaccharides, glyceraldehyde, glycerol, dehydrated sugars, furfural, hydroxymethyl furfural, levulinic acid or esters and carbohydrates.

4. The system of claim 1, wherein said zeolite catalyst is selected from the group consisting of ZSM-12, ZSM-35, ZSM-38, Pentasil zeolite, and any combinations thereof.

5. The system of claim 1, wherein said separator is selected from the group consisting of a gas-liquid separator, liquid-liquid separator, three-phase separator, horizontal separator, vertical separator, tubular separator, rotary separator, turbine separator, centrifugal separator, and any combinations thereof.

6. The system of claim 1, wherein said reformer comprises a catalyst selected from the group consisting of nickel impregnated aluminum oxide ($Ni/Al_2O_3$), nickel impregnated magnesium oxide (Ni/MgO), platinum impregnated aluminum oxide ($Pt/Al_2O_3$), platinum impregnated magnesium oxide (Pt/MgO), catalyst impregnated ceramic pellets, modified ceramics, metal foils, and any combinations thereof.

7. The system of claim 1, wherein said hydrotreater comprises a catalyst selected from the group consisting of nickel, aluminum, hafnium, platinum, palladium, ruthenium, Raney nickel, palladium (II) acetate trimer, palladium (II) chloride, sodium tetrachloropalladate (II), tetrakis(triphenylphosphine)palladium (0), dihydrogen hexachloroplatinate (IV), platinum (II) chloride, platinum (IV) chloride, potassium tetrachloroplatinate (II), chloro(1,5-cyclooctadiene)rhodium (I) dimer, chlorotris(triphenylphosphine)rhodium (I), rhodium (II) acetate dimer, rhodium (III) chloride hydrate, ruthenium (III) chloride trihydrate, iridium (III) chloride hydrate, osmium (VIII) tetroxide, rhenium carbonyl ($Re_2(CO)_{10}$), organophosphines, nickel, copper impregnated zinc oxide (Cu/ZnO), copper impregnated chromium oxide (Cu/Cr), nickel aluminum oxide ($Ni/Al_2O_3$), palladium aluminum oxide ($Pd/Al_2O_3$), cobalt molybdenum (CoMo), nickel molybdenum (NiMo), and combinations thereof.

8. The system of claim 1, wherein said organic stream comprises gasoline-range hydrocarbons and greater than 50% by weight of said gasoline-range hydrocarbons are aromatic hydrocarbons.

9. The process of claim 2, wherein said feedstock comprises at least one of monosaccharides, disaccharides, polysaccharides, glyceraldehyde, glycerol, dehydrated sugars, furfural, hydroxymethyl furfural, levulinic acid or esters and carbohydrates.

10. The process of claim 2, wherein said zeolite catalyst is selected from the group consisting of ZSM-12, ZSM-35, ZSM-38, Pentasil zeolite, and any combinations thereof.

11. The process of claim 2, wherein said separator is selected from the group consisting of a gas-liquid separator, liquid-liquid separator, three-phase separator, horizontal separator, vertical separator, tubular separator, rotary separator, turbine separator, centrifugal separator, and any combinations thereof.

12. The process of claim 2, wherein said reformer comprises a catalyst selected from the group consisting of nickel impregnated aluminum oxide (Ni/Al$_2$O$_3$), nickel impregnated magnesium oxide (Ni/MgO), platinum impregnated aluminum oxide (Pt/Al$_2$O$_3$), platinum impregnated magnesium oxide (Pt/MgO), catalyst impregnated ceramic pellets, modified ceramics, metal foils, and any combinations thereof.

13. The process of claim 2, wherein said hydrotreater comprises a catalyst selected from the group consisting of nickel, aluminum, hafnium, platinum, palladium, ruthenium, nickel, palladium (II) acetate trimer, palladium (II) chloride, sodium tetrachloropalladate (II), tetrakis(triphenylphosphine)palladium (0), dihydrogen hexachloroplatinate (IV), platinum (II) chloride, platinum (IV) chloride, potassium tetrachloroplatinate (II), chloro(1,5-cyclooctadiene)rhodium (I) dimer, chlorotris(triphenylphosphine)rhodium (I), rhodium (II) acetate dimer, rhodium (III) chloride hydrate, ruthenium (III) chloride trihydrate, Iridium (III) chloride hydrate, osmium (VIII) tetroxide, rhenium carbonyl (Re$_2$(CO)$_{10}$), organophosphines, nickel, copper impregnated zinc oxide (Cu/ZnO), copper impregnated chromium oxide (Cu/Cr), nickel aluminum oxide (Ni/Al$_2$O$_3$), palladium aluminum oxide (Pd/Al$_2$O$_3$), cobalt molybdenum (CoMo), nickel molybdenum (NiMo), and combinations thereof.

14. The process of claim 2, wherein greater than 50% by weight of said gasoline-range hydrocarbons are aromatic hydrocarbons.

* * * * *